United States Patent
Kosecoff

(10) Patent No.: US 11,756,685 B2
(45) Date of Patent: Sep. 12, 2023

(54) ULTRAVIOLET LIGHT SENSOR AND METHOD TO ACHIEVE TARGETED VITAMIN D LEVELS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 292 days.

(21) Appl. No.: 16/909,879

(22) Filed: Jun. 23, 2020

(65) Prior Publication Data
US 2021/0398669 A1 Dec. 23, 2021

(51) Int. Cl.
*G16H 50/20* (2018.01)
*A61B 5/00* (2006.01)
*G01J 1/42* (2006.01)
*G01J 1/02* (2006.01)

(52) U.S. Cl.
CPC ............. *G16H 50/20* (2018.01); *A61B 5/443* (2013.01); *G01J 1/429* (2013.01); *G01J 1/0219* (2013.01)

(58) Field of Classification Search
CPC ......... A61B 5/157; A61B 5/441; A61B 5/443; A61B 5/44; G01J 2001/4276; G01J 2001/4266; G01J 1/42; G01J 1/4209; G01J 1/429; G01J 1/00; G01J 1/02; G01J 1/0219; G16H 50/00; G16H 50/02
See application file for complete search history.

(56) References Cited

U.S. PATENT DOCUMENTS

| | | | | |
|---|---|---|---|---|
| 9,383,256 B2* | 7/2016 | Lian | ............ | G01J 1/44 |
| 9,470,577 B2* | 10/2016 | Lian | ............ | G06F 1/163 |
| 9,551,611 B2* | 1/2017 | Oliver | ............ | G01J 1/0219 |
| 9,707,243 B2* | 7/2017 | Ali | ............ | A61K 36/53 |
| 9,753,182 B1* | 9/2017 | Bennouri | ............ | G01J 1/0219 |
| 9,816,857 B2* | 11/2017 | Rastegar | ............ | G01J 1/0271 |
| 9,823,120 B2* | 11/2017 | Lian | ............ | G01J 1/429 |
| 9,880,052 B2* | 1/2018 | Dumont | ............ | G06F 1/3287 |
| 10,060,787 B2* | 8/2018 | Balooch | ............ | G01J 1/50 |
| 10,463,133 B2* | 11/2019 | Sun | ............ | G01J 1/429 |

(Continued)

OTHER PUBLICATIONS

"QSun | A Smart Sun Protection Wearable by Comfable Inc.," Kickstarter <https://www.kickstarter.com/projects/comfable/qsun/description> [retrieved Aug. 10, 2021]; "QSun | A Smart Sun Protection Wearable by Comfable Inc.," Kickstarter Updates <https://www.kickstarter.com/projects/comfable/qsun/posts> [retrieved Aug. 10, 2021].

(Continued)

*Primary Examiner* — John R Lee
(74) *Attorney, Agent, or Firm* — Christensen O'Connor Johnson Kindness PLLC

(57) ABSTRACT

The computer system and computer-implemented method of generating and providing skin care product recommendations to a subject, wherein the method comprises determining, by a computing device, a UV-B exposure of the subject; determining, by the computing device, a vitamin D intake due to the UV-B exposure; determining, by the computing device, a target vitamin D of the subject; and providing, by the computing device, a skin care product recommendation to the subject when the vitamin D intake due to the UV-B exposure is less than the vitamin D target of the subject.

8 Claims, 4 Drawing Sheets

(56) References Cited

U.S. PATENT DOCUMENTS

| | | | | |
|---|---|---|---|---|
| 10,527,490 | B2* | 1/2020 | Dumont | G06F 1/1632 |
| 10,648,858 | B2* | 5/2020 | Lian | G01J 1/44 |
| 10,823,608 | B2* | 11/2020 | Wei | G01J 1/429 |
| 10,922,397 | B2* | 2/2021 | Toumazou | G06F 1/163 |
| 10,939,025 | B2* | 3/2021 | Hu | G01J 1/4228 |
| 10,957,807 | B2* | 3/2021 | Kotru | G01J 1/44 |
| 11,118,968 | B1* | 9/2021 | Lian | G01T 1/02 |
| 11,311,744 | B2* | 4/2022 | Moffat | G16H 20/40 |
| 2010/0226946 | A1* | 9/2010 | Alberts | A61K 35/60 424/59 |
| 2015/0041663 | A1* | 2/2015 | Oliver | G01W 1/00 250/372 |
| 2018/0308997 | A1* | 10/2018 | Kotru | H01L 31/0465 |
| 2018/0353770 | A1* | 12/2018 | Moffat | A61N 5/0616 |
| 2019/0204146 | A1* | 7/2019 | Wei | G01J 1/0219 |
| 2020/0100997 | A1* | 4/2020 | Soler | A61K 41/0061 |
| 2020/0143027 | A1* | 5/2020 | Toumazou | A61B 5/0022 |
| 2020/0368559 | A1* | 11/2020 | Poutiatine | A61B 5/442 |
| 2020/0376292 | A1* | 12/2020 | Moffat | A61N 5/0616 |
| 2021/0398669 | A1* | 12/2021 | Kosecoff | G16H 20/70 |
| 2022/0028564 | A1* | 1/2022 | Kosecoff | G01J 1/0219 |
| 2022/0083638 | A1* | 3/2022 | Toumazou | H04W 4/80 |
| 2022/0178744 | A1* | 6/2022 | Kosecoff | G01J 1/429 |

OTHER PUBLICATIONS

"Violet: Track Your Sun Exposure and Vitamin D Levels by Ultra, Inc." Kickstarter <https://www.kickstarter.com/projects/342933744/violet-optimize-your-sun-experience/description> [retrieved Aug. 10, 2021]; < https://www.kickstarter.com/projects/342933744/violet-optimize-your-sun-experience/posts> [retrieved Aug. 10, 2021].

Sadat-Ali, M. et al., "Topical Delivery of Vitamin D3: a Randomized Controlled Pilot Study," International Journal of Biomedical Science, pp. 21-24, Mar. 1, 2014: <https://www.ncbi.nlm.nih.gov/pmc/articles/PMC3976443/pdf/IJBS-10-21.pdf> [retrieved Aug. 10, 2021].

Sadat-Ali et al. "Topical Delivery of Vitamin D3: a Randomized Controlled Pilot Study", International Journal of Biomedical Science, vol. 10, No. 1, pp. 21-24 (2014), (No month).

L'Oreal Research and Innovation, "My Skin UV : a battery-free wearable sun safety sensor by La Roche-Posay", Nov. 26, 2018, https://www.loreal.com/media/news/2018/nov/my-skin-track-uv, (No month).

Ola Engelsen, "Calculated Ultraviolet Exposure Levels for a Healthy Vitamin D Status", Norwegian Institute for Air Research, Version 1.0, 2005, https://fastrt.nilu.no/VitD-ez_quartMED.html, (No month).

Webb, A.R. and O. Engelsen, "Calculated Ultraviolet Exposure Levels for a Healthy Vitamin D Status", Photochemistry and Photobiology, 82(6), pp. 1697-1703 (2006), (No month).

* cited by examiner

ULTRAVIOLET LIGHT SENSOR AND METHOD TO ACHIEVE TARGETED VITAMIN D LEVELS

SUMMARY

A UV-B sensor device and App to help a subject maintain or achieve targeted vitamin D levels through sun exposure and transdermal application of vitamin D. A method executed by a computing device receives UV exposure data from a wearable UV sensor, retrieves the estimated vitamin D intake through the measured UV-B exposure, retrieves a target vitamin D for the user, and recommends a skin care product to make up any deficit of vitamin D by comparing the target vitamin D to the vitamin D intake. Alternatively, when the vitamin D intake through UV-B exposure is equal to or greater than the target vitamin D, the computing device may also warn the user of the risk of overexposure to UV radiation.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Vitamin D is necessary for our body's health. Vitamin D helps to absorb calcium to form strong bones. Vitamin D can enter a body through several sources, such as through food or vitamin supplements, and even the body can produce vitamin D when exposed to sunlight or other UV light. Doctors often recommend a certain amount of sun exposure for our body to produce vitamin D.

UV radiation is the part of the electromagnetic spectrum that has a wavelength from 100 to 400 nm. UV radiation is further divided into UV-C (short wave), UV-B (medium wave) and UV-A (long wave). The ozone layer blocks most of the UV-B radiation reaching the earth's surface and practically all of the UV-C radiation. UV-B has a wavelength from about 280 to 315 nm. UV-B is responsible for producing vitamin D in the body. When UV-B is absorbed by a person's skin, a set of reactions is started that leads to the synthesis of vitamin D. Therefore, knowing the amount of sun exposure, and particularly the amount of UV-B exposure, is important to determine or not a person is meeting the daily, weekly, or monthly intake of vitamin D and whether further exposure only puts the person at risk to the negative effects overexposure entails.

Because calculating the amount of exposure to give the required amount of vitamin D intake for any given subject is a complicated function based on blood test results, weather conditions, time of day, skin type, and/or previous exposure history, this disclosure provides an easy method of determining whether a subject is below, above (at risk of sun burn), or at their targeted hourly/daily/weekly/etc. dose of sun exposure. The method further provides recommendations on supplementing the lack of skin exposure to the sun with vitamin D skin care products that can deliver vitamin D through the dermal route.

This disclosure relates to a system and a computer-implemented method or App that intelligently calculates and advises, for example, when to get sun exposure, when to go inside (at risk of burn), and when to apply Vitamin D product based on, for example, weather conditions, time of day, skin type, previous exposure history (hourly/daily/weekly/etc.), and target Vitamin D levels.

Figure 1:
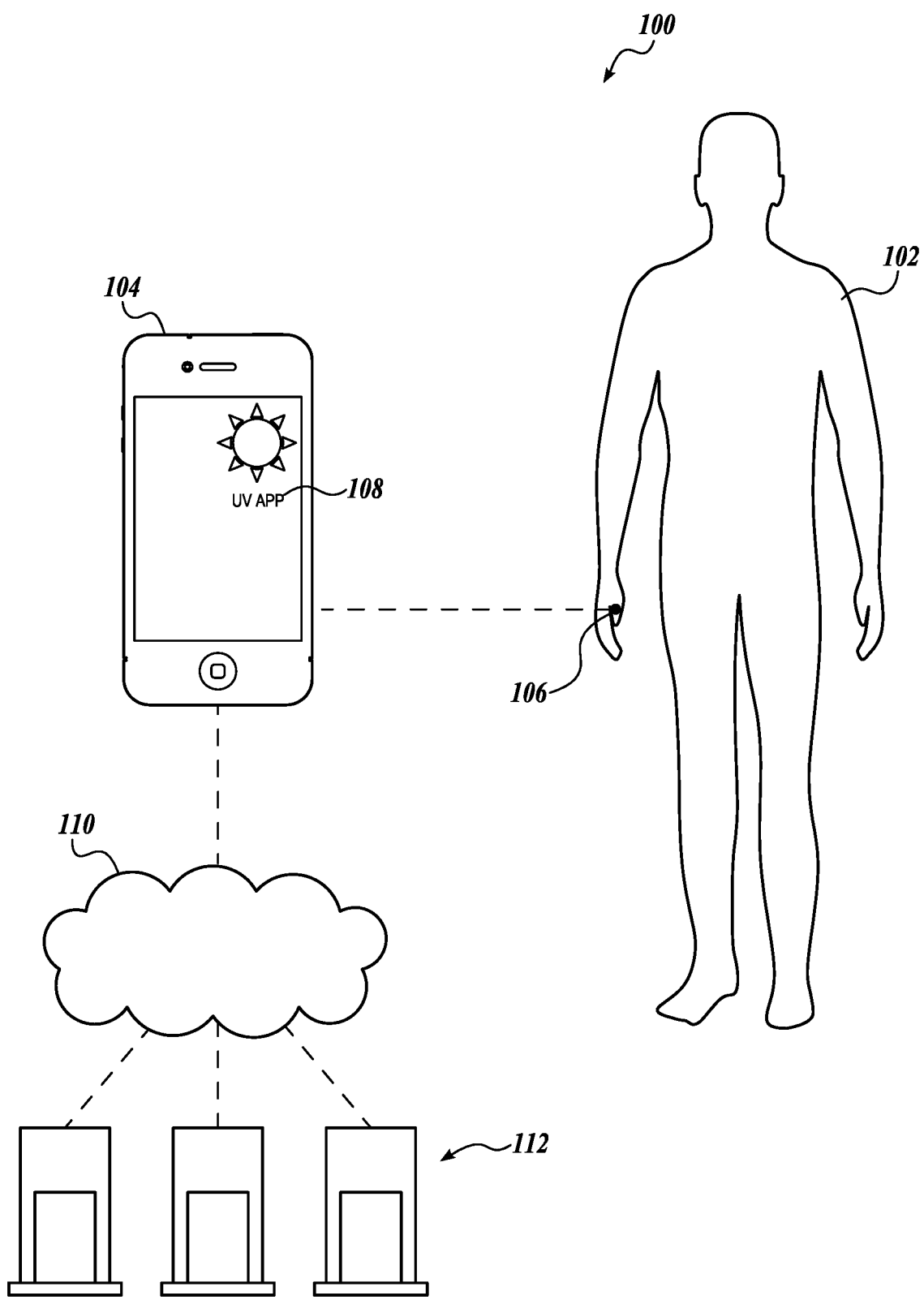
FIG. 1 a schematic diagram that illustrates a non-limiting example embodiment of a system for generating and providing product recommendations to a subject according to various aspects of the present disclosure.

FIG. 1 is a schematic diagram that illustrates a non-limiting example embodiment of a system 100 for generating and providing vitamin D product recommendations to a subject 102 according to various aspects of the present disclosure. In the system 100, the subject 102 interacts with a mobile computing device 104. In some embodiments, the mobile computing device 104 may be used to receive measured UV exposure data from a wearable UV sensor 106 on the subject 102 that that is used to calculate the amount of UV-B exposure.

Existing technologies already provide a wearable UV sensor 106 that measures the amount of UV exposure, from which a mobile computing device, such as mobile computing device 104, can calculate a personal daily safe UV dose based on skin type and minimal erythema dose. See, for example, US Publication 20190204146. Such technologies may go so far as to recommend sunscreen products designed to provide protection against UV for the particular subject. In some embodiments, the wearable UV sensor 106 is minimally obtrusive and may be worn on a fingernail.

In some embodiments, the mobile computing device 104 is capable of performing a computer-implemented method or App. The subject may start the computer-implemented method by touching the icon 108 on a touch-sensitive display of the mobile computing device 104. The computer-implemented method is further described in connection with FIG. 4.

In some embodiments, the mobile computing device 104 is connected to a remote server computer system 112 comprised of one or more server computers via a network, such as the Internet 110. The network may include any suitable networking technology, including but not limited to a wireless communication technology (including but not limited to Wi-Fi, WiMAX, Bluetooth, 2G, 3G, 4G, 5G, and LTE), a wired communication technology (including but not limited to Ethernet, USB, and FireWire), or combinations thereof.

Figure 2:
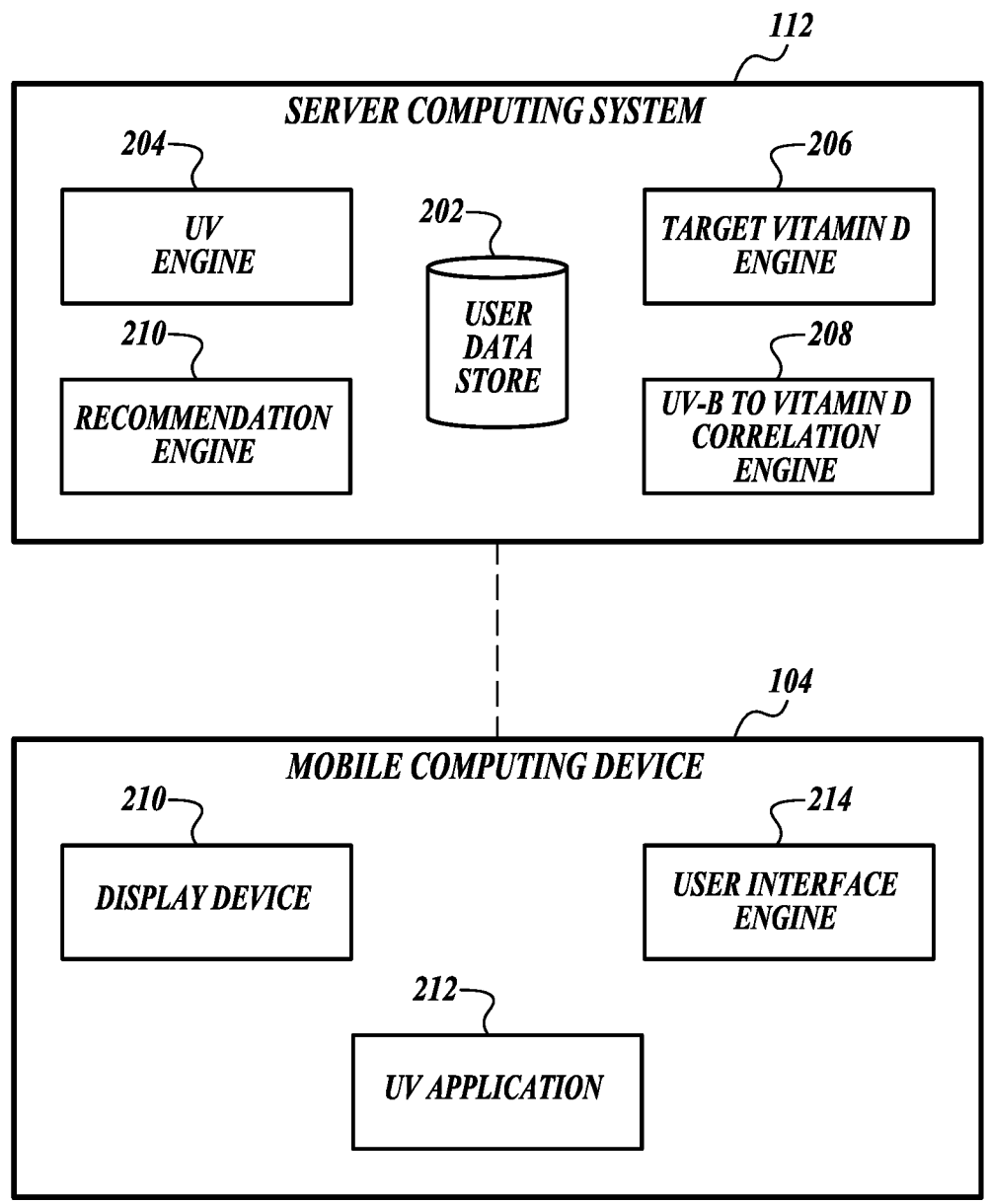
FIG. 2 is a block diagram that illustrates a non-limiting example embodiment of a system that includes a mobile computing device and a server computing device according to various aspects of the present disclosure.

FIG. 2 is a block diagram that illustrates a non-limiting example embodiment of a system that includes the mobile computing device 104 and a server computing system 112 according to various aspects of the present disclosure. In some embodiments, the mobile computing device 104 may be a smartphone. In some embodiments, the mobile computing device 104 may be any other type of computing device having the illustrated components, including but not limited to a tablet computing device or a laptop computing device. In some embodiments, the mobile computing device 104 may not be mobile, but may instead by a stationary computing device such as a desktop computing device. In some embodiments, the illustrated components of the mobile computing device 104 may be within a single housing. In some embodiments, the illustrated components of the mobile computing device 104 may be in separate housings that are communicatively coupled through wired or wireless connections. The mobile computing device 104 also includes other components that are not illustrated, including but not limited to one or more processors, a non-transitory computer-readable medium, a power source, and one or more communication interfaces.

As shown, the mobile computing device 104 includes, at least, a display device 210, a UV Application 212 (or UV App), and a user interface engine 214.

In some embodiments, the display device 210 is an LED display, an OLED display, or another type of display for presenting a user interface. In some embodiments, the display device 210 may be combined with or include a touch-sensitive layer, such that a subject 102 may interact with a user interface presented on the display device 210 by touching the display. In some embodiments, a separate user interface device, including but not limited to a mouse, a keyboard, or a stylus, may be used to interact with a user interface presented on the display device 210.

In some embodiments, the user interface engine 214 is configured to present a user interface on the display device 210 when opening the UV App 212. The UV App 212 will cause the user interface engine 214 to display a plurality of user interfaces on the display device 210 relating to a computer-implemented method used for the gathering and display of information, including providing recommendations for transdermal vitamin D supplements. For example, the user interface engine 214 can present the subject with a questionnaire that is useful to elicit information for determining the subject's sun exposure, the subject's vitamin D target, and also provides graphs of cumulative UV-B exposure over a day, week, month, etc., the amount of vitamin D intake from such exposure over a day, week, month, graph the target vitamin D, and other options and information.

In some embodiments, the server computing system 112 includes one or more computing devices that each include one or more processors, non-transitory computer-readable media, and network communication interfaces that are collectively configured to provide the components illustrated below. In some embodiments, the one or more computing devices that make up the server computing system 112 may be rack-mount computing devices, desktop computing devices, or computing devices of a cloud computing service.

In some embodiments, the server computing system 112 is configured to perform data analytics for determining the sun exposure amount, the vitamin D intake amount, and the vitamin D target amount. The mobile computing device 104 is configured to connect to the server computing system 112 in a cloud computing environment. As shown, the server computing system 112 includes a user data store 202, a UV engine, 204, a target vitamin D engine 206, a recommendation engine 208, and a UV-B to vitamin D correlation engine.

In some embodiments, the user data store 202 is configured to store records for each subject 102 that uses the system. The records may include medical records, such as age, weight, blood test results, historical vitamin D levels, skin phototype, target vitamin D amount, product recommendations, and/or other information collected or determined by the system.

In some embodiments, the UV engine 204 may be configured to process the data acquired by the UV sensor 106. For example, the exposure amount of UV-B is calculated based on energy captured by a UV-B photodiode or LED.

In some embodiments, the target vitamin D engine 206 is configured to calculate the subject's daily, weekly, or monthly target vitamin D levels. Target Vitamin D levels are can be based on blood test results or general principles related to typical human conditions. A questionnaire may be presented to the subject at the start to gather information that is used in the estimation of the target vitamin D.

In some embodiments, the UV-B to vitamin D correlation engine 208 is configured to estimate the amount of vitamin D intake by the body based on the amount of UV-B exposure, such as through sunlight or other UV source, measured by the UV sensor 106. Existing technologies are available that predict the vitamin D intake due to measured UV-B exposure. Correlations from the simple to the complex can be used that predict that amount of vitamin D intake from UV-B exposure based on some of the following factors: time of year and location relating to the sun altitude, skin phototype I to VI relating to skin color, time of day relating to the sun altitude, sky condition as it relates to the amount of cloud cover, ozone layer thickness, elevation, ground surface type relating to the reflectivity of light, and the subject's biological and physiological factors, such as age, weight, current vitamin D level in the blood, etc. See Webb, A. R. and O. Engelsen (2006) Calculated Ultraviolet Exposure Levels for a Healthy Vitamin D Status. Photochemistry and Photobiology. 82(6), 1697-1703 (https://fas-trt.nilu.no/VitD-ez_quartMED.html).

In some embodiments, the amount of vitamin D intake from UV-B exposure and the target amount of vitamin D are given as the vitamin D level found in the subject's blood, for example, in units of nmol/l. In some embodiments, the amount of vitamin D found in supplements, such as vitamin D that can be administered transdermally or orally, is given in International Units (IU) or micrograms (mcg or μg).

In some embodiments, the amount of vitamin D intake from UV-B exposure is defined as vitamin $D_{UV}$ and the target vitamin D is defined as vitamin $D_T$. Therefore, in some embodiments, the recommended amount of vitamin D supplement or vitamin $D_S$ can the amount of vitamin D that will make up the deficit of vitamin D between $D_T$ and $D_{UV}$ over a given period of time. For example, in one model, the amount of vitamin D supplement, vitamin $D_S$, can be proportional to the difference of $D_T$ minus $D_{UV}$. Determining the amount of vitamin $D_S$ may also take into consideration biological and physiological factors that can influence the absorption of vitamin D into the blood especially if administered transdermally.

In some embodiments, the recommended dose of vitamin D supplement, $D_S$, is given on a per unit of time basis. For example, vitamin D doses can be recommended on 1*a* daily or weekly basis. For example, doses of vitamin D supplement may include 1,000 IU to 2,000 IU per day or 5,000 IU per week In some embodiments, the recommended dose of vitamin D supplement, $D_S$, is only an amount to increase the vitamin D in the blood level when the subject is found to be deficient in vitamin D.

In some embodiments, the recommended dose of vitamin D supplement, $D_S$, is not proportional to the difference of $D_T$ minus $D_{UV}$, and the dose is any amount of vitamin D supplement as provided by the supplement manufacturer.

In some embodiments, the amount of Vitamin $D_S$ supplement may also be administered orally instead of transdermally or by a combination of oral and transdermal administration. The amount of vitamin D that is absorbed into the blood either through transdermal or oral administration may be based on empirical testing of the supplement done by the vitamin D supplement manufacturer.

In some embodiments, the recommendation engine 210 is configured to generate recommendations of, at least, skin care products for transdermally administering vitamin D to increase the vitamin D in the blood of the subject based on comparing the target vitamin D level to the vitamin D produced through UV exposure. Skin care products for transdermally administering vitamin D may be provided as creams, spray liquids, patches, and the like. Transdermal vitamin D skin care products may also include other ingredients, such as moisturizers, antioxidants, hyaluronic acid, collagen, carriers such as oil and water, and the like.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

"Data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 3:
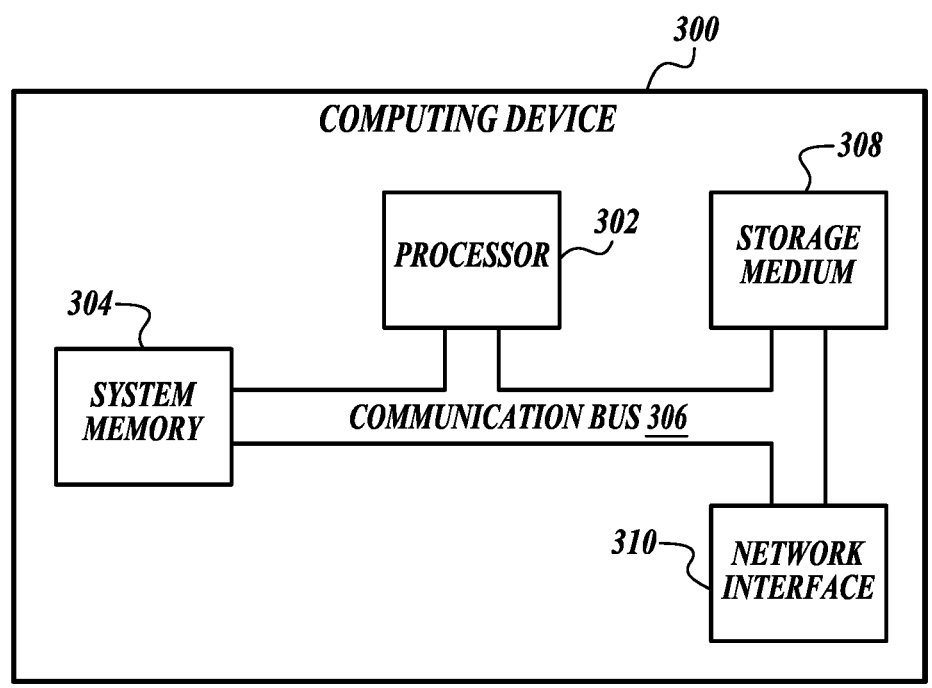
FIG. 3 is a block diagram that illustrates a non-limiting example embodiment of a computing device appropriate for use as a computing device with embodiments of the present disclosure.

FIG. 3 is a block diagram that illustrates aspects of an exemplary computing device 300 appropriate for use as a mobile computing device of the present disclosure. While multiple different types of computing devices were discussed above, the exemplary computing device 300 describes various elements that are common to many different types of computing devices. While FIG. 3 is described with reference to a mobile computing device, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 300 may be any one of any number of currently available or yet to be developed devices.

In its most basic configuration, the computing device 300 includes at least one processor 302 and a system memory 304 connected by a communication bus 306. Depending on the exact configuration and type of device, the system memory 304 may be volatile or nonvolatile memory, such as read only memory ("ROM"), random access memory ("RAM"), EEPROM, flash memory, or similar memory technology. Those of ordinary skill in the art and others will recognize that system memory 304 typically stores data and/or program modules that are immediately accessible to and/or currently being operated on by the processor 302. In this regard, the processor 302 may serve as a computational center of the computing device 300 by supporting the execution of instructions.

As further illustrated in FIG. 3, the computing device 300 may include a network interface 310 comprising one or more components for communicating with other devices over a network. Embodiments of the present disclosure may access basic services that utilize the network interface 310 to perform communications using common network protocols. The network interface 310 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 310 illustrated in FIG. 3 may represent one or more wireless interfaces or physical communication interfaces described and illustrated above with respect to particular components of the computing device 300.

In the exemplary embodiment depicted in FIG. 3, the computing device 300 also includes a storage medium 308. However, services may be accessed using a computing device that does not include means for persisting data to a local storage medium. Therefore, the storage medium 408 depicted in FIG. 3 is optional. In any event, the storage medium 308 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 304 and storage medium 308 depicted in FIG. 3 are merely examples of computer-readable media.

Suitable implementations of computing devices that include a processor 302, system memory 304, communication bus 306, storage medium 308, and network interface 310 are known and commercially available. For ease of illustration and because it is not important for an understanding of the claimed subject matter, FIG. 3 does not show some of the typical components of many computing devices. In this regard, the computing device 300 may include input devices, such as a keyboard, keypad, mouse, microphone, touch input device, touch screen, tablet, and/or the like. Such input devices may be coupled to the computing device 300 by wired or wireless connections including RF, infrared, serial, parallel, Bluetooth, Bluetooth low energy, USB, or other suitable connections protocols using wireless or physical connections. Similarly, the computing device 300 may also include output devices such as a display, speakers, printer, etc. Since these devices are well known in the art, they are not illustrated or described further herein.

Figure 4:
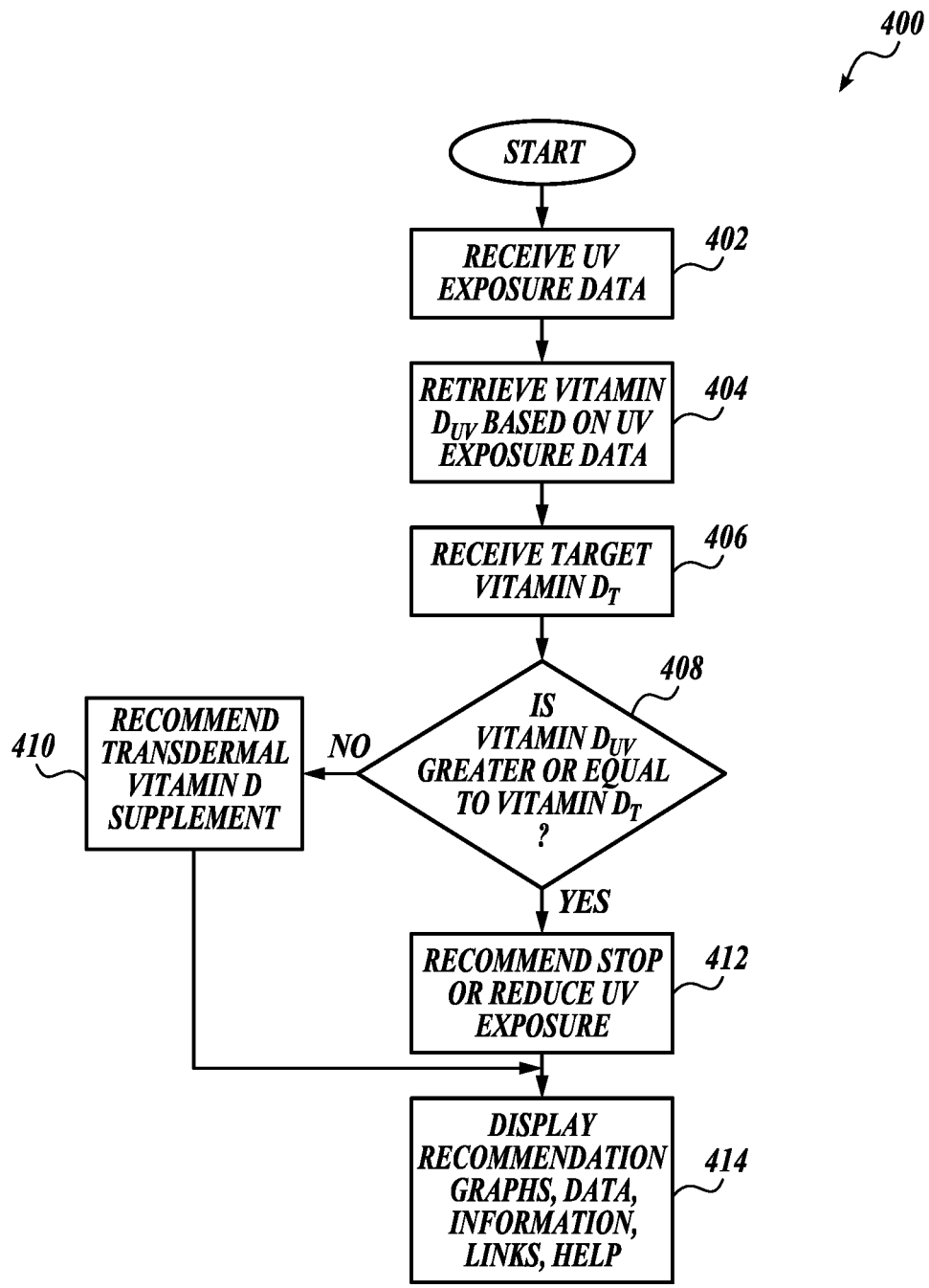
FIG. 4 is a flowchart that illustrates a non-limiting example embodiment of a method of generating and providing recommendations to a subject according to various aspects of the present disclosure.

FIG. 4 is a flowchart that illustrates a non-limiting example embodiment of a method of generating and providing recommendations of skin care products that supplement vitamin D for a subject. The method 400 may be implemented, in one example, by the mobile computing device 104 alone or in combination with one or more server computing devices 112.

In some embodiments, the method may be performed in part by the mobile computing device 104 and in part by the remote server computer system 112. In some embodiments, the mobile computing device 104 is configured to upload data regarding the subject to an external system or server (such as a cloud-based system). Such data may include the user profile.

The computer-implemented method 400 may start by clicking on the UV App icon 108 on the display of the mobile computing device 104 to open the UV App 212. From the start block, the UV App 212 proceeds to block 402, where the UV App 212 receives UV-B data from the wearable device 106 on the subject 102.

Depending on the sensor 106, data can be processed by the sensor 106 or the mobile computing device 104. In some embodiments, the subject 102 scans the sensor 106 with the mobile computing device 104 to establish a connection between the sensor 106 and the mobile computing device 104. Communication pairing is performed between the sensor 106 and the mobile computing device when the two devices are within an acceptable wireless communication range of each other. In some embodiments, the sensor 106 includes RFID and antenna for the subject to obtain the data wirelessly.

In some embodiments the sensor 106 contains a UV sensitive LED that will induce electronic current proportional to UV exposure. The amount of UV exposure can then be converted and stored as voltage, which is a measurement of cumulative UV exposure over time. UV exposure can be reported on a per unit of time basis, such as daily, weekly, monthly, etc.

The voltage is read each time as the subject scans the sensor 106. The scanned voltage data is converted by the UV engine 204 into a UV-A dosage based on the calibrated correlations. In some embodiments, UV-B exposure is then calculated using a pre-computed lookup table that gives the conversion factor as function of the column amount of ozone in the atmosphere and solar zenith angle (SZA). SZA is determined based on GPS location and time.

In some embodiments, the UV engine 204 can communicate with the User Data Store 202 that keeps track of the subject's GPS location and time, for example. The subject's latitude, longitude, and time can also be used to extract the forecast ozone amount from satellite-measurements to be used by the UV-B to Vitamin D Correlation Engine 208. The UV-A and UV-B doses calculated by the UV engine 204 represents the amount of UV exposure that subject was exposed to during a period between two consecutive scans. The subject can follow their UV exposure over time and determine whether they exceed their personal daily safe UV dose and risk level. The UV engine 204 can keep a running total of UV-B exposure in any increments of time, such as by the hour, day, week, month, or year.

From block 402, the UV App 212 proceeds to block 404. In block 404, the UV App 212 retrieves the vitamin $D_{UV}$ indicative of the vitamin D intake that corresponds to the UV-B exposure determined by the UV engine 204. The UV-B to vitamin D correlation engine 208 determines the estimated vitamin $D_{UV}$ intake.

In some embodiments, the UV-B to vitamin D correlation engine 208 uses a model predictive of vitamin $D_{UV}$ intake. For example, correlations have been modeled that are based on some or all of the following factors: time of year and location relating to the sun altitude, subject's skin phototype I to VI relating to skin color, time of day relating to the sun altitude, sky condition as it relates to the amount of cloud cover, ozone layer thickness, subject's elevation, ground surface type relating to the reflectivity of light, and the subject's biological and physiological factors, such as age, weight, current vitamin D level in the blood, etc. When the vitamin D intake is retrieved, the UV Application 212 moves from block 404 to block 406.

In block 406, the mobile computing device 104 receives the target vitamin $D_T$. The target vitamin D engine 206 determines the target vitamin D, $D_T$. The target vitamin D, $D_T$, is the amount of vitamin D that is sought to be provided through UV-B exposure. In some embodiments, the target vitamin D engine 206 estimates the level of vitamin D in the blood of the subject and how far away the estimated vitamin D level is from the ideal vitamin D level. A representative ideal vitamin D level in the blood can be at least 75 nmol/l. The target vitamin D, $D_T$, therefore, is the difference between the ideal vitamin D level minus the current estimate of vitamin D in the subject's blood. This difference is then sought to be made up by UV-B exposure. When UV-B exposure is not sufficient to achieve the target vitamin D, then, the UV App 212 provides recommendations for a vitamin D supplement.

In some embodiments, the target vitamin D, $D_T$, level can be retrieved from various sources or may be calculated based on the subject's biological and physiological factors, such as blood test results and general principles related to typical human conditions. A model can also be used to predict the vitamin D in the subject's blood. Since vitamin D is also constantly being replenished and depleted in a subject's body, a model can adjust the estimated blood vitamin D based on diet and rate of depletion. The estimated blood vitamin D level may also be adjusted based on age, weight, recent blood tests, etc. A questionnaire at the start may be used to elicit information from the subject regarding diet and other factors affecting blood levels of vitamin D. From block 406, the UV App 212 proceeds to block 408.

In block 408, the mobile computing device 104 determines whether or not the vitamin $D_{UV}$ is greater or equal to the vitamin $D_T$. That is, whether the vitamin D intake through UV-B exposure is equal to or greater than the target vitamin D for the subject.

If the answer is no, meaning that UV exposure has not resulted in sufficient intake of vitamin D, and the subject is deficient in vitamin D, the UV App 212 can recommend a skin care product that transdermally administers vitamin D, and can present the subject with a protocol or regimen. The recommendation can be based on the deficiency of the vitamin D, the subject's medical history, and the subject's biological and physiological factors.

If the answer is yes, meaning that UV exposure has resulted in more intake of vitamin D in the subject than the target vitamin D, $D_T$, the UV App 212 enters block 412. In block 412, the UV App 212 can recommend to stop or reduce UV exposure. In some embodiments, the daily safe UV exposure dose is calculated based on the skin phototype and minimal erythema dose (MED). In some embodiments, the skin phototype is determined by a questionnaire completed by the subject at the start. The UV engine 204 can determine the daily safe UV dose.

From block 410 or block 412, the UV App 212 enters block 414. In block 414, the mobile computing device 104 can display the skin care product recommendation. The user interface engine 214 can determine the appropriate user interface displayed by the mobile computing device 104. In addition, the user interface engine 214 can also provide graphs, data, information, warnings, useful links, and help.

In some embodiments, the user interface engine 214 may create a display on the mobile computing device 104 with an indication of the user risk in percentage form, along with a category label such as "low", "moderate," or "high." A graph may also be displayed that tracks the UV exposure level over time for the day, and keeps track of the vitamin D intake predicted from the UV exposure and graph the vitamin D intake along with the target vitamin D.

In some embodiments, the user interface engine 214 may create tutorials on how to use the skin care products. The user interface engine 214 may create and download protocols for a regimen or routine. The user interface engine 214 may can coach, track usage and compare the tracked usage to the protocol, the regimen, and the routine.

Additionally, the user interface engine 214 can be used to make a purchase of any products related to skincare or UV protection.

Representative embodiments are given by the following examples.

In one embodiment, a computer-implemented method of generating and providing skin care product recommendations to a subject, the method comprises determining, by a computing device, a UV-B exposure of the subject; determining, by the computing device, a vitamin D intake due to the UV-B exposure; determining, by the computing device, a target vitamin D of the subject; and providing, by the computing device, a skin care product recommendation to the subject when the vitamin D intake due to the UV-B exposure is less than the vitamin D target of the subject.

In one embodiment, the computer-implemented method further comprises providing a notification that the subject is at risk of UV overexposure when the vitamin D intake due to the UV-B exposure is greater than the target vitamin D.

In one embodiment, the skin care product recommendation is a transdermally applied vitamin D supplement.

In one embodiment, the computer-implemented method further comprises tracking the vitamin D intake due to UV exposure.

In one embodiment, the computer-implemented method further comprises tracking the vitamin D intake due to UV exposure along with the target vitamin D.

In one embodiment, the target vitamin D is calculated by estimating the level of vitamin D in the subject's blood, and subtracting the estimated level of vitamin D in the subject's blood from an ideal vitamin D level in blood.

In one embodiment, a computing device is configured to: determine a UV-B exposure of the subject; determine a vitamin D intake due to the UV-B exposure; determine a target vitamin D of the subject; and provide a skin care product recommendation to the subject when the vitamin D intake due to the UV-B exposure is less than the vitamin D target of the subject.

In one embodiment, the computing device is further configured to provide a notification that the subject is at risk of UV overexposure when the vitamin D intake due to the UV-B exposure is greater than the target vitamin D.

In one embodiment, the skin care product recommendation is a transdermally applied vitamin D supplement.

In one embodiment, the computing device is further configured to track the vitamin D intake due to UV exposure.

In one embodiment, the computing device is further configured to track the vitamin D intake due to UV exposure along with the target vitamin D.

In one embodiment, the target vitamin D is calculated by estimating the level of vitamin D in the subject's blood, and subtracting the estimated level of vitamin D in the subject's blood from an ideal vitamin D level in blood.

In one embodiment, a system comprises: a UV sensor engine including computational circuitry configured to determine a UV-B exposure amount of the subject; a UV-B to vitamin D correlation engine including computational circuitry configured to determine a vitamin D intake due to the UV-B exposure; a target vitamin D engine including computational circuitry configured to determine a target vitamin D of the subject; and a recommendation engine including computational circuitry configured to provide a skin care product recommendation to the subject when the vitamin D intake due to the UV-B exposure is less than the vitamin D target of the subject.

In one embodiment, the recommendation engine includes computational circuitry configured to provide a notification that the subject is at risk of UV overexposure when the vitamin D intake due to the UV-B exposure is greater than the target vitamin D.

In one embodiment, the skin care product recommendation is a transdermally applied vitamin D supplement.

In one embodiment, the system comprises a user interface engine including computational circuitry configured to track the vitamin D intake due to UV exposure.

In one embodiment, the system comprises a user interface engine including computational circuitry configured to track the vitamin D intake due to UV exposure along with the target vitamin D.

In one embodiment, the target vitamin D is calculated by estimating the level of vitamin D in the subject's blood, and subtracting the estimated level of vitamin D in the subject's blood from an ideal vitamin D level in blood.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of generating and providing skin care product recommendations to a subject, the method comprising:
   storing an amount of UV exposure over time as a voltage on a UV sensor;
   scanning the UV sensor with a computing device to convert the voltage into a UV-A dosage;
   determining, by the computing device, a UV-B exposure of the subject based on the UV-A dosage;
   determining, by the computing device, a vitamin D intake due to the UV-B exposure;
   determining, by the computing device, a target vitamin D of the subject; and
   providing, by the computing device, a skin care product recommendation to the subject when the vitamin D intake due to the UV-B exposure is less than the vitamin D target of the subject, wherein the skin care product recommendation is a transdermally applied vitamin D supplement, wherein the target vitamin D is calculated by estimating the level of vitamin D in the subject's blood, and subtracting the estimated level of vitamin D in the subject's blood from an ideal vitamin D level in blood.

2. The computer-implemented method of claim 1, further comprising providing a notification that the subject is at risk of UV overexposure when the vitamin D intake due to the UV-B exposure is greater than the target vitamin D.

3. The computer-implemented method of claim 1, further comprising tracking the vitamin D intake due to UV exposure.

4. The computer-implemented method of claim 1, further comprising tracking the vitamin D intake due to UV exposure along with the target vitamin D.

5. A system, comprising:
   a UV sensor, wherein the UV sensor stores an amount of UV exposure over time as a voltage;
   a computing device that wirelessly communicates with the UV sensor to convert the voltage into a UV-A dosage;
   a UV sensor engine including computational circuitry configured to:
      determine a UV-B exposure amount of the subject based on the UV-A dosage;
   a UV-B to vitamin D correlation engine including computational circuitry configured to:
      determine a vitamin D intake due to the UV-B exposure;
   a target vitamin D engine including computational circuitry configured to:
      determine a target vitamin D of the subject; and
   a recommendation engine including computational circuitry configured to:
      provide a skin care product recommendation to the subject when the vitamin D intake due to the UV-B exposure is less than the vitamin D target of the subject, wherein the skin care product recommendation is a transdermally applied vitamin D supplement, wherein the target vitamin D is calculated by estimating the level of vitamin D in the subject's blood, and subtracting the estimated level of vitamin D in the subject's blood from an ideal vitamin D level in blood.

6. The system of claim 5, wherein the recommendation engine includes computational circuitry configured to:
   provide a notification that the subject is at risk of UV overexposure when the vitamin D intake due to the UV-B exposure is greater than the target vitamin D.

7. The system of claim 5, comprising a user interface engine including computational circuitry configured to:
   track the vitamin D intake due to UV exposure.

8. The system of claim 5, comprising a user interface engine including computational circuitry configured to:
   track the vitamin D intake due to UV exposure along with the target vitamin D.

* * * * *